United States Patent
Miyazawa

(10) Patent No.: US 9,636,270 B2
(45) Date of Patent: May 2, 2017

(54) FINGER ASSIST DEVICE

(71) Applicant: Seiko Epson Corporation, Tokyo (JP)

(72) Inventor: Osamu Miyazawa, Shimosuwa-machi (JP)

(73) Assignee: Seiko Epson Corporation (JP)

(*) Notice: Subject to any disclaimer, the term of this patent is extended or adjusted under 35 U.S.C. 154(b) by 191 days.

(21) Appl. No.: 14/202,686

(22) Filed: Mar. 10, 2014

(65) Prior Publication Data
US 2014/0288664 A1 Sep. 25, 2014

(30) Foreign Application Priority Data
Mar. 25, 2013 (JP) ................... 2013-061543

(51) Int. Cl.
A61H 1/02 (2006.01)
A61F 2/58 (2006.01)
A61F 2/68 (2006.01)
A61F 5/01 (2006.01)

(52) U.S. Cl.
CPC .......... *A61H 1/0288* (2013.01); *A61F 2/586* (2013.01); *A61F 2/68* (2013.01); *A61F 5/013* (2013.01); *A61H 2201/1635* (2013.01); *A61H 2201/5061* (2013.01); *A61H 2205/065* (2013.01); *A61H 2205/067* (2013.01)

(58) Field of Classification Search
CPC ............... A61H 1/0288; A61H 1/0285; A61H 2201/1635; A61H 2201/5061; A61H 2205/067; A61H 2205/065; A61F 2/586
See application file for complete search history.

(56) References Cited

U.S. PATENT DOCUMENTS

| 2004/0212278 | A1  | 10/2004 | Miyazawa |
| 2006/0094989 | A1* | 5/2006  | Scott ................ A61F 2/54 601/5 |
| 2007/0228875 | A1  | 10/2007 | Miyazawa |
| 2009/0160291 | A1  | 6/2009  | Miyazawa |
| 2010/0041521 | A1* | 2/2010  | Ingvast ............. A61H 1/0288 482/49 |

(Continued)

FOREIGN PATENT DOCUMENTS

| JP | 11-309184 A   | 11/1999 |
| JP | 2002-345861 A | 12/2002 |

(Continued)

*Primary Examiner* — Justine Yu
*Assistant Examiner* — Kathrynn Lyddane
(74) *Attorney, Agent, or Firm* — Harness, Dickey & Pierce, P.L.C.

(57) ABSTRACT

A finger assist device is formed by rotatably connecting a plurality of units in a finger bending direction and a finger spreading direction. The unit is worn on a finger by nipping the finger with a nipping part from the pad and the back of the finger, and a drive force is controlled by detecting a first contact force between the finger pad and the nipping part and a second contact force between the finger back and the nipping part. Since the intention of the wearer of the finger assist device appears in the first contact force and the second contact force, the drive force of the finger assist device is appropriately controlled according to the wearer's intention, and thereby, bending and spreading of the finger may be appropriately assisted.

17 Claims, 10 Drawing Sheets

(56) References Cited

U.S. PATENT DOCUMENTS

| | | | |
|---|---|---|---|
| 2010/0249675 A1* | 9/2010 | Fujimoto | A61H 1/0285 601/40 |
| 2010/0262291 A1 | 10/2010 | Takesue et al. | |
| 2010/0305717 A1* | 12/2010 | Tong | A61H 1/0285 623/64 |
| 2011/0071664 A1* | 3/2011 | Linn | B25J 9/0006 700/213 |
| 2012/0029399 A1* | 2/2012 | Sankai | A61B 5/04888 601/40 |
| 2012/0279342 A1 | 11/2012 | Yasukawa et al. | |

FOREIGN PATENT DOCUMENTS

| | | |
|---|---|---|
| JP | 2004-260990 A | 9/2004 |
| JP | 2007-267482 A | 10/2007 |
| JP | 2009-066696 A | 4/2009 |
| JP | 2009-201648 A | 9/2009 |
| JP | 2010-082342 A | 4/2010 |
| JP | 2010-188018 A | 9/2010 |
| JP | 2011-067609 A | 4/2011 |
| JP | 2011-115248 A | 6/2011 |
| JP | 2012-235622 A | 11/2012 |
| JP | 2012-253990 A | 12/2012 |

\* cited by examiner

FINGER ASSIST DEVICE

BACKGROUND

1. Technical Field

The present invention relates to a finger assist device.

2. Related Art

Devices for assisting finger movement worn on hands of people with difficulty in bending and spreading their fingers due to accidents and diseases, people with weakened grips, and elderly people with less power due to aging have been proposed (See, e.g., JP-A-2002-345861 and JP-A-2011-115248).

However, it is hard to detect a person's intention to bend or spread (herein, "spread" means to unbend or straighten) a finger, and accordingly, in both of the above proposals, there has been a problem in that it has been difficult to appropriately assist the bending movement or spreading movement of the finger.

SUMMARY

An advantage of some aspects of the invention is to provide a technology that may appropriately assist bending movement or spreading movement of a finger by detecting a person's intention to bend or spread the finger.

A finger assist device according to an aspect of the invention employs the following configuration. That is, a finger assist device worn on a finger and assisting movement of bending the finger includes a plurality of units (links or bodies) rotatably connected at joints in a bending direction in which the finger bends and a spreading direction in which the finger spreads in an opposite direction to the bending direction, suppose that a side facing an object to be grasped by the finger is a pad of the finger and an opposite side of the pad of the finger is a back of the finger, a nipping part (e.g., a nipper, band or clasp) provided in each of the plurality of units and nipping (e.g., pinching, squeezing or gripping) the pad of the finger and the back of the finger, at least one of a first sensor that detects a first contact force generated between the nipping part and the pad of the hand finger and a second sensor that detects a second contact force generated between the nipping part and the back of the hand finger provided in the nipping part, a drive part connected to the unit and rotationally driving the unit in the direction in which the finger bends or the direction in which the finger spreads, and a drive force control part that controls a drive force of the drive part for rotationally driving the unit based on the first contact force and the second contact force.

The finger assist device according to the aspect of the invention assists the movement of the finger by rotationally driving the connected plurality of units in the direction in which the finger bends or the direction in which the finger spreads. Here, the unit is attached to the finger by nipping the finger with the nipping part from the pad and the back of the finger. Note that "finger pad" refers to a side at which the finger faces an object when the finger is bent for grasping the object. Further, "finger back" refers to an opposite side to the finger pad. Further, the drive force is controlled by detecting the contact force between the finger pad and the nipping part (first contact force) and the contact force between the finger back and the nipping part (second contact force). The details will be described later, and, since the intention of a wearer of the finger assist device appears in the first contact force and the second contact force, the drive force of the finger assist device is appropriately controlled according to the wearer's intention in this manner, and thereby, bending movement and spreading movement of the finger may be appropriately assisted.

In the finger assist device according to the aspect of the invention, in the state in which the unit is rotationally driven in the bending direction of the finger, the drive force may be increased and decreased in the following manner. That is, the drive force may be increased if the first contact force is larger than the second contact force and the drive force may be decreased if the first contact force is smaller than the second contact force.

The case where the first contact force is larger than the second contact force in the state in which the unit is rotationally driven in the bending direction of the finger is considered as the case where the wearer tends to further bend the finger. In contrast, the case where the first contact force is smaller than the second contact force is considered as the case where the wearer tends to weaken the force for bending the finger. Therefore, the contact forces are detected in the above described manner, and thereby, the drive force may be increased or decreased according to the wearer's intention.

In the finger assist device according to the aspect of the invention, if the difference between the first contact force and the second contact force when the unit is rotationally driven in the bending direction of the finger is smaller than a predetermined threshold value, the drive force may not be increased or decreased. That is, in the state in which the unit is rotationally driven in the bending direction of the finger, if the first contact force is larger than the second contract force by a first increase-side threshold value or more, the drive force is increased, and if the second contact force is larger than the first contract force by a first decrease-side threshold value or more, the drive force is decreased. Further, in the state in which the unit is rotationally driven in the bending direction of the finger, if the first contact force is larger than the second contract force and an excess amount of the first contact force with respect to the second contact force is less than the first increase-side threshold value, or if the second contact force is larger than the first contact force and an excess amount of the second contact force with respect to the first contact force is less than the first decrease-side threshold value, the drive force may be maintained. Note that the threshold value at the side at which the drive force is increased (first increase-side threshold value) and the threshold value at the side at which the drive force is decreased (first decrease-side threshold value) are sufficient as long as they may be individually set, and the first increase-side threshold value and the first decrease-side threshold value may be set to the same value.

According to the configuration, an increase and decrease of the drive force with an increase and decrease of the first contact force and the second contact force by the slight movement of the finger not intended by the wearer (e.g., trembling of the finger) may be avoided. As a result, the bending movement and the spreading movement of the finger may be stably assisted according to the wearer's intention.

In the finger assist device according to the aspect of the invention, in the state in which the unit is rotationally driven in the spreading direction, the drive force may be increased and decreased in the following manner. That is, the drive force may be decreased if the first contact force is larger than the second contact force and the drive force may be increased if the first contact force is smaller than the second contact force.

The case where the first contact force is larger than the second contact force in the state in which the unit is rotationally driven in the spreading direction is considered as the case where the wearer tends to weaken the force for spreading the finger. In contrast, the case where the first contact force is smaller than the second contact force is considered as the case where the wearer tends to further spread the finger. Therefore, by controlling the drive force in the above described manner, the drive force may be increased or decreased according to the wearer's intention.

In the finger assist device according to the aspect of the invention, if the difference between the first contact force and the second contact force when the unit is rotationally driven in the spreading direction is smaller than a predetermined threshold value, the drive force may not be increased or decreased. That is, in the state in which the unit is rotationally driven in the spreading direction, if the second contact force is larger than the first contract force by a second increase-side threshold value or more, the drive force is increased, and if the first contact force is larger than the second contract force by a second decrease-side threshold value or more, the drive force is decreased. Furthermore, in the state in which the unit is rotationally driven in the spreading direction, if the second contact force is larger than the first contract force and an excess amount of the second contact force with respect to the first contact force is less than the second increase-side threshold value, or if the first contact force is larger than the second contact force and an excess amount of the first contact force with respect to the second contact force is less than the second decrease-side threshold value, the drive force may be maintained. Note that the threshold value at the side at which the drive force is increased (second increase-side threshold value) and the threshold value at the side at which the drive force is decreased (second decrease-side threshold value) are sufficient as long as they may be individually set, and the second increase-side threshold value and the second decrease-side threshold value may be set to the same value.

According to the configuration, an increase and decrease of the drive force with an increase and decrease of the first contact force and the second contact force by the slight movement of the finger not intended by the wearer (e.g., trembling of the finger) may be avoided. As a result, the bending movement and the spreading movement of the finger may be stably assisted according to the wearer's intention.

In the finger assist device according to the aspect of the invention, the second increase-side threshold value may be set to be a smaller value than the first increase-side threshold value and the second decrease-side threshold value may be set to be a smaller value than the first decrease-side threshold value.

Generally, during spreading of the finger, the force of the finger is smaller than that at bending. Therefore, by setting the second increase-side threshold value to be the smaller value than the first increase-side threshold value and the second decrease-side threshold value to be the smaller value than the first decrease-side threshold value, at the time of spreading the finger, the movement of the finger may be assisted from when the finger is subject to the smaller force than that at bending.

In the finger assist device according to the aspect of the invention, the first sensor and the second sensor may be provided especially in the nipping part of the unit at the tip end side of the finger among the units. Note that, in this case, the first sensor and the second sensor may be provided in the nipping parts of the other units.

When the finger is bent or spread, the movement of the finger is larger toward the tip end of the finger. Therefore, by providing the first sensor and the second sensor especially in the nipping part of the unit at the tip end side of the finger among the units, the wearer's intention may be sensitively sensed and the movement of the finger may be appropriately assisted.

In the finger assist device according to the aspect of the invention, a first nipping portion provided on the finger pad may be formed more deformably than a second nipping portion provided on the finger back.

According to the configuration, when the wearer grasps an object, a feeling of grasping the object is transmitted to the finger pad of the wearer via the first nipping portion, and a finger assist device that may easily grasp an object may be realized.

In the finger assist device according to the aspect of the invention, a vibrator formed to contain a piezoelectric material may be used as the drive part for rotationally driving the unit. As the vibrator, a bending vibration-type piezo-actuator may be preferably used.

According to the configuration, a thinner vibrator enables a thinner finger assist device. Further, the vibrator is pressed against a connecting member for use, and thus, while the connecting member is not rotationally driven, the vibrator functions as a brake for preventing rotation of the connecting member. Accordingly, even when the connecting member is not driven by the vibrator, the finger does not lean back due to the load.

BRIEF DESCRIPTION OF THE DRAWINGS

Embodiments of the invention will be described with reference to the accompanying drawings, wherein like numbers reference like elements.

DESCRIPTION OF EXEMPLARY EMBODIMENTS

Figure 1A:
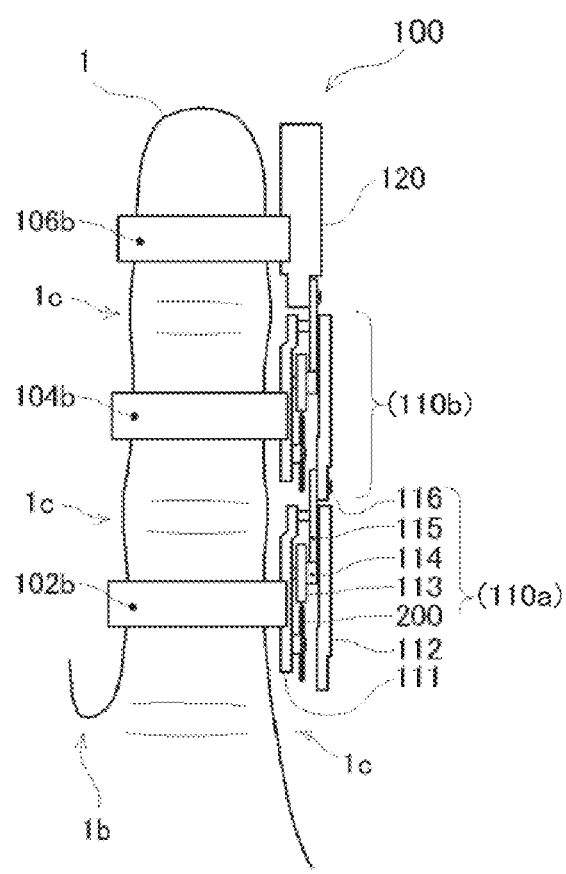
FIGS. 1A to 1C are overall views of a finger assist device of an embodiment.
Figure 1B:
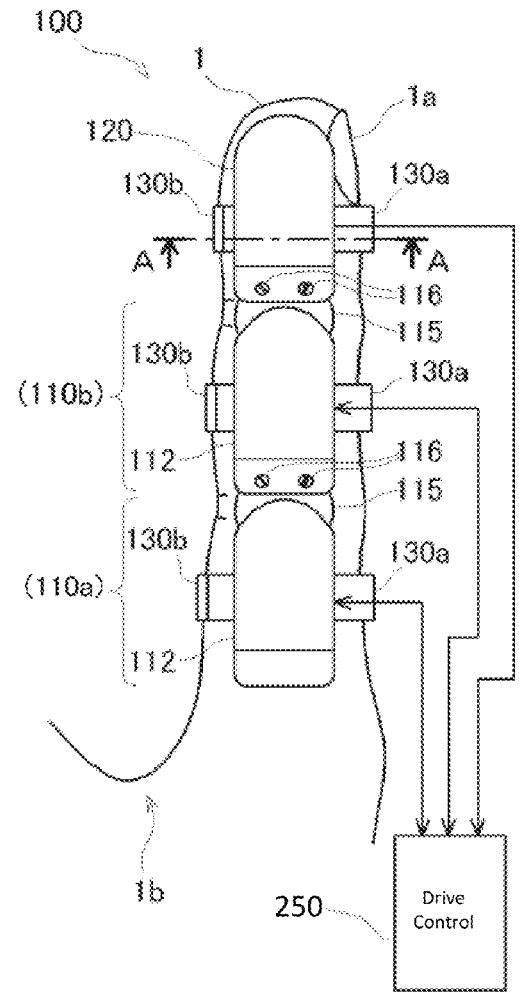

FIGS. 1A and 1B are explanatory diagrams showing a state in which a finger assist device 100 of an embodiment is worn on a finger 1 (index finger) of a human hand. FIG. 1A shows the state seen from a pad of the finger 1, and FIG. 1B shows the state seen from a side surface side of the finger 1. Further, the sign 1a shown in FIGS. 1A and 1B denotes a nail of the finger 1, the sign 1b denotes a fork of the finger 1, and the signs 1c denote joints of the finger 1. Note that "finger pad" refers to a side at which the finger 1 faces an object when the finger 1 is bent for grasping the object. Further, "finger back" refers to an opposite side to the finger pad. Note that, in the embodiment, the case where the device is worn on the finger 1 of a human hand is explained, however, the device may be worn on a toe or on a finger or a toe of a non-human such as an animal.

As illustrated, the finger assist device 100 of the embodiment includes a plurality of (two in the illustrated example) series-connected drive units 110, and a finger tip unit 120 connected to a tip end. The same two drive units 110 are used, and, when it is necessary to distinguish the units, they are respectively referred to as drive units 110a, 110b as shown in FIGS. 1A and 1B. Further, the drive unit 110 of the embodiment corresponds to "unit" in the invention.

As shown in FIG. 1A, the drive unit 110 includes a first member 111 provided at the side of the finger 1, a second member 112 provided at the opposite side to the finger 1 with the first member 111 in between, a rotor 113 having a disc shape and provided between the first member 111 and the second member 112, a piezoelectric motor 200 that rotates the rotor 113, a first spur gear 114 that rotates with the rotor 113, a second spur gear 115 fitted with the first spur gear 114, and connecting screws 116 that connect the first spur gear 114 to the second member 112 of the adjacent drive unit 110. Therefore, the respective drive units 110 may be freely attached and detached by fastening and loosening the connecting screws 116. Further, the piezoelectric motor 200 is connected to a drive control unit 250 that controls the driving direction and the drive force of the piezoelectric motor 200 by supplying drive signals. Note that the piezoelectric motor 200 of the embodiment corresponds to "drive part" or "vibrator" in the invention, and the drive control part 250 of the embodiment corresponds to a "drive force control part" in the invention.

Further, a first nipping portion 130b and a second nipping portion 130a (e.g., clasps) are provided in each of the first member 111 of the drive unit 110a, the first member 111 of the drive unit 110b, and the finger tip unit 120, and the first nipping portion 130b nips (e.g., squeezes or grips) the finger 1 from the pad of the finger 1 and the second nipping portion 130a nips the finger 1 from the back of the finger 1. Accordingly, as shown in FIGS. 1A and 1B, the finger 1 is nipped by the first nipping portions 130b and the second nipping portions 130a provided in the drive units 110a, 110b and the finger tip unit 120, and thereby, the finger assist device 100 of the embodiment may be worn on the finger 1. Furthermore, the second nipping portion 130a is formed using a non-deformable material such as metal or hard resin, and the first nipping portion 130b is formed using a deformable material such as soft resin. Accordingly, even when grasping an object with the finger assist device 100 worn on the finger 1, the wearer may feel a sense of grasping the object with the pad of the finger 1 via the first nipping portions 130b. Note that the first nipping portion 130b and the second nipping portion 130a of the embodiment correspond to a "nipping part".

Figure 1C:
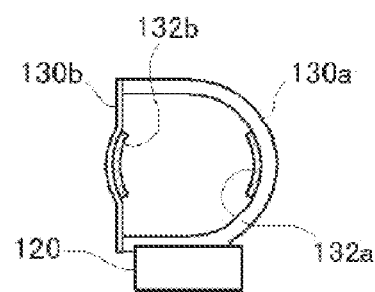

FIG. 1C shows a sectional view of the finger tip unit 120 cut along A-A. As illustrated, a first sensor 132b is provided in a position in contact with the pad of the finger 1 in the first nipping portion 130b of the finger tip unit 120. Further, a second sensor 132a is provided in a position in contact with the back of the finger 1 in the second nipping portion 130a of the finger tip unit 120. Accordingly, when the finger assist device 100 of the embodiment is worn on the finger 1, the pad of the finger 1 is in contact with and lightly pressed against the first sensor 132b, and the back of the finger 1 is in contact with and lightly pressed against the second sensor 132a.

The output from the first sensor 132b and the second sensor 132a is supplied to the drive control part 250. Further, the drive control part 250 drives the piezoelectric motor 200 based on the output from the first sensor 132b and the second sensor 132a. This point will be explained in detail later. Note that, in the embodiment, the explanation that the first sensor 132b and the second sensor 132a are attached only to the first nipping portion 130b and the second nipping portion 130a of the finger tip unit 120 is made, however, the first sensor 132b and the second sensor 132a may be attached to the first nipping portions 130b and the second nipping portions 130a of the drive units 110a, 110b.

Figure 2A:
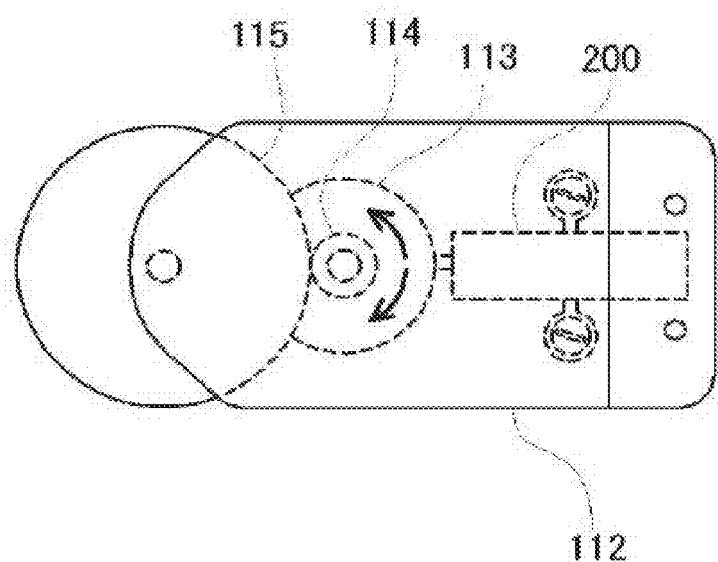
FIGS. 2A to 2C are explanatory diagrams showing a structure of a drive unit of the finger assist device.
Figure 2B:
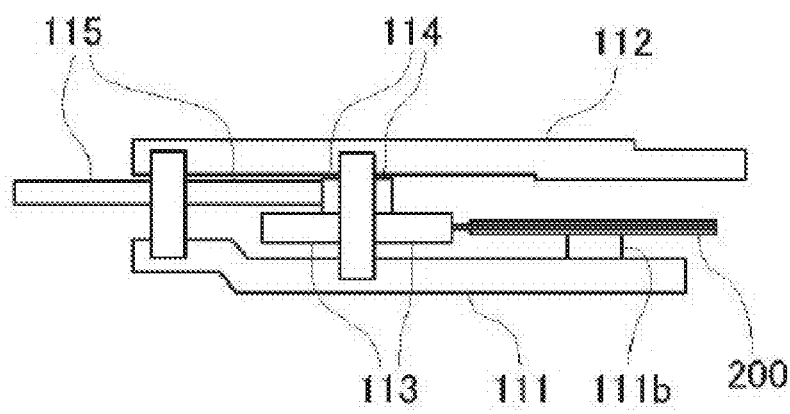
Figure 2C:
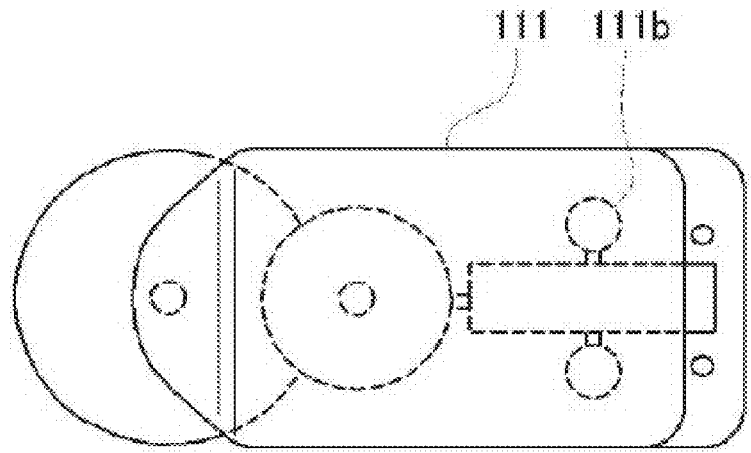

FIGS. 2A to 2C are explanatory diagrams showing a detailed structure of the drive unit 110. Note that, in FIGS. 2A to 2C, the illustration of attachment portions 102, 104 is omitted. FIG. 2A is a front view of the drive unit 110 seen from the opposite side to the side worn on the finger 1 (the side of the second member 112), FIG. 2B is a sectional view of the drive unit 110 in the center position, and FIG. 2C is a rear view of the drive unit 110 seen from the side worn on the finger 1 (the side of the first member 111).

In the first member 111, bosses 111b having cylindrical shapes are projected in two locations and the piezoelectric motor 200 is fixed (e.g., screwed) on the top surfaces of the bosses 111b. The structure of the piezoelectric motor 200 will be described later. Further, the disc-shaped rotor 113 is attached between the first member 111 and the second member 112, and the first spur gear 114 is coaxially attached to the rotor 113 and integrally rotates with the rotor 113. Furthermore, the second spur gear 115 is fitted with the first spur gear 114. Therefore, when the rotor 113 is rotated using the piezoelectric motor 200, the first spur gear 114 rotates with the rotor 113 and the second spur gear 115 rotates. The second spur gear 115 has the larger number of teeth than that of the first spur gear 114. Accordingly, the rotation of the first spur gear 114 is decelerated (therefore, energized) and transmitted to the second spur gear 115.

Figure 3:
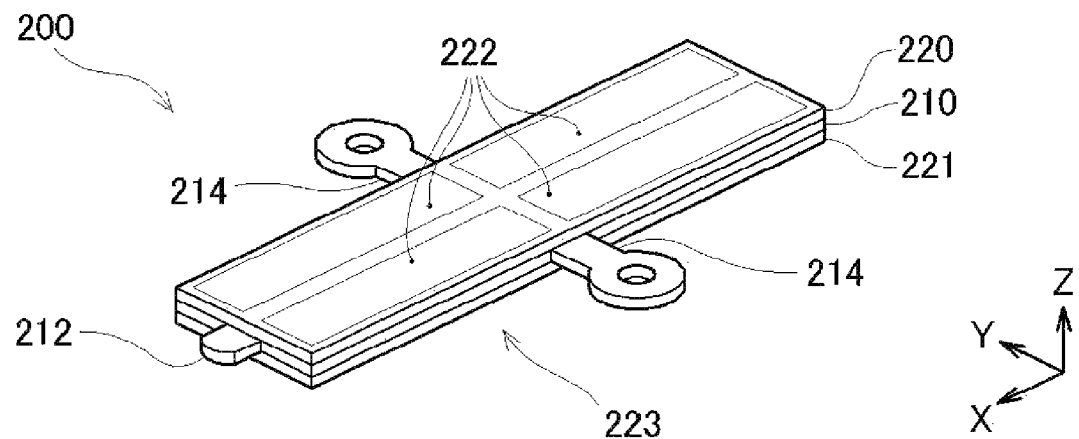
FIG. 3 is a perspective view showing a structure of a piezoelectric motor.

FIG. 3 is a perspective view showing the structure of the piezoelectric motor 200. As illustrated, the piezoelectric motor 200 has a multilayered structure in which a shim plate 210 formed by a metal flat plate is sandwiched and bonded between two piezoelectric devices (front piezoelectric device 220, rear piezoelectric device 221) formed in plate-like shapes and containing a piezoelectric material. Note that, below, the longitudinal direction of the piezoelectric motor 200 will be referred to as "X-direction". Further, as shown in the drawing, the lateral direction of the piezoelectric motor 200 orthogonal to the X-direction will be referred to as "Y-direction", and the thickness direction of the piezoelectric motor 200 orthogonal to the X-direction and the Y-direction will be referred to as "Z-direction".

Front electrodes 222 for applying voltages to the front piezoelectric device 220 are provided on the surface (upper surface) opposite to the surface of the front piezoelectric device 220 in contact with the shim plate 210. As shown in FIG. 3, the four rectangular front electrodes 222 are provided to split the upper surface of the front piezoelectric device 220 into four in a lattice shape. Further, though not illustrated, similarly, four rectangular rear electrodes 223 are provided on the surface (lower surface) opposite to the surface of the rear piezoelectric device 221 in contact with the shim plate 210 to split the lower surface into four in a lattice shape. Furthermore, the metal shim plate 210 has a role not only to reinforce the piezoelectric devices (front piezoelectric device 220, rear piezoelectric device 221) but also as a common electrode for applying voltages to the front piezoelectric device 220 and the rear piezoelectric device 221, and is grounded.

A convex portion 212 is provided at the end in the longitudinal direction (X-direction) of the piezoelectric motor 200. Further, a pair of support portions 214 for supporting the piezoelectric motor 200 to be urged toward the side at which the convex portion 212 is provided are provided on both side surfaces facing in the lateral direction (Y-direction) of the piezoelectric motor 200. The convex portion 212 and the support portions 214 are formed integrally with the shim plate 210.

Figure 4A:
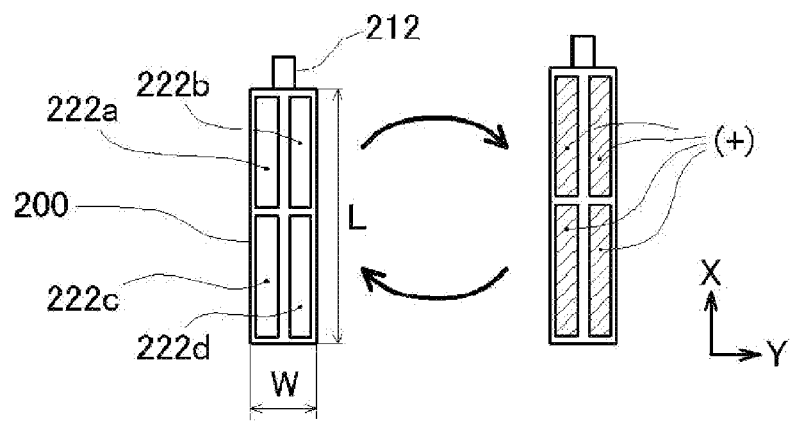
FIGS. 4A to 4C are explanatory diagrams showing an operation principle of the piezoelectric motor.
Figure 4B:
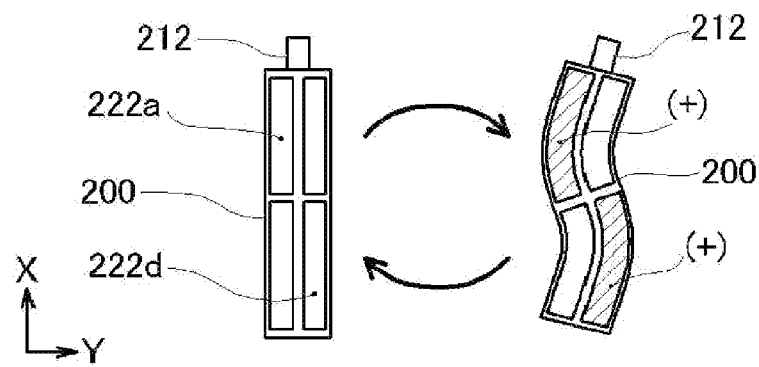
Figure 4C:
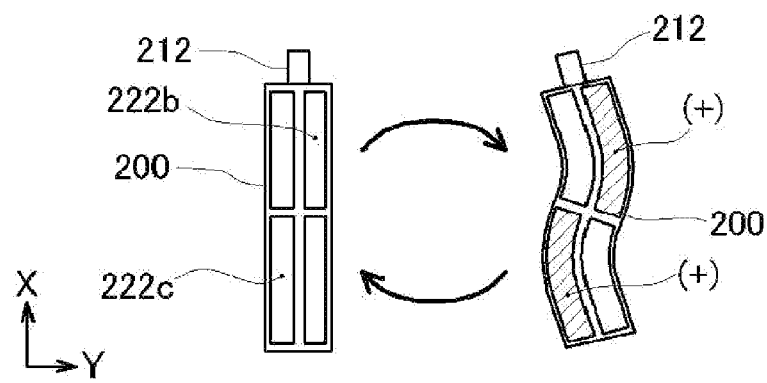

FIGS. 4A to 4C are explanatory diagrams showing an operation principle of the piezoelectric motor 200. The piezoelectric motor 200 operates by elliptic motion of the convex portion 212 of the piezoelectric motor 200 when voltages are applied to the front electrodes 222 and the rear electrodes 223 of the piezoelectric motor 200 with a constant period. The convex portion 212 of the piezoelectric motor 200 makes elliptic motion for the following reason. Note that the front electrodes 222 provided on the front piezoelectric device 220 and the rear electrodes 223 provided on the rear piezoelectric device 221 are plane-symmetric with respect to the X-Y plane and basically the same and, here, the explanation will be made by taking the front electrodes 222 as examples.

First, the piezoelectric devices containing the piezoelectric material (front piezoelectric device 220, rear piezoelectric device 221) have properties of expanding when positive voltages are applied. Therefore, as shown in FIG. 4A, when application of positive voltages to all of the four front electrodes 222 and non-application of the voltages are repeated at specific frequencies, the piezoelectric motor 200 (front electrodes 222) may produce a kind of resonance phenomenon of expanding and contracting in the longitudinal direction (X-direction). The movement of the piezoelectric motor 200 repeating expanding and contracting in the longitudinal direction (X-direction) is called "longitudinal vibration", and the directions in which the piezoelectric motor 200 expands and contracts (±X-directions in the drawing) are called "stretching directions".

Further, as shown in FIG. 4B or 4C, with the two front electrodes 222 diagonally located to each other as sets (a set of the front electrode 222a and the front electrode 222d or a set of the front electrode 222b and the front electrode 222c), when voltages at specific frequencies are applied, a kind of resonance phenomenon that the end of the piezoelectric motor 200 (front piezoelectric device 220) in the longitudinal direction (X-direction) (the part provided with the convex portion 212) oscillates in the lateral direction (Y-direction) on the drawing may be produced. For example, as shown in FIG. 4B, when the positive voltages are applied to the set of the front electrode 222a and the front electrode 222d with a constant period, the end of the piezoelectric motor 200 in the longitudinal direction repeats movement of moving to the right. Furthermore, as shown in FIG. 4C, when the positive voltages are applied to the set of the front electrode 222b and the front electrode 222c with a constant period, the end of the piezoelectric motor 200 in the longitudinal direction repeats movement of moving to the left. The movement of the piezoelectric motor 200 is called "bending vibration". Below, the directions in which the piezoelectric motor 200 bends and vibrates (±Y-directions in the drawing) are called "bending directions".

Further, by appropriate selection of the properties of the front piezoelectric device 220 and the dimensions (width W, length L, thickness T) of the front piezoelectric device 220, resonance in "bending vibration" may induce the resonance in "longitudinal vibration" at the same time. As a result, when the voltages are applied to the set of the front electrode 222a and the front electrode 222d in the form shown in FIG. 4B, the end of the piezoelectric motor 200 (the part provided with the convex portion 212) makes movement of describing an ellipse (elliptic motion) clockwise on the drawing. Furthermore, when the voltages are applied to the set of the front electrode 222b and the front electrode 222c in the form shown in FIG. 4C, the end of the piezoelectric motor 200 makes elliptic motion counterclockwise on the drawing. Completely the same applies to the rear piezoelectric device 221 as the piezoelectric device 220.

The piezoelectric motor 200 drives a driven member using the elliptical motion. That is, the elliptical motion is generated with the convex portion 212 of the piezoelectric motor 200 pressed against the driven member. Then, the convex portion 212 repeats the movement of moving from left to right (or from right to left) while being pressed against the driven member when the piezoelectric motor 200 expands, and returning to the original position while being apart from the driven member when the piezoelectric motor 200 contracts. As a result, the driven member is driven in one direction by the frictional force from the convex portion 212.

The piezoelectric motor 200 mounted on the drive unit 110 of the embodiment is set with the convex portion 212 pressed against the rotor 113 (see FIGS. 2A to 2C). Accordingly, when the piezoelectric motor 200 is driven, the rotor 113 and the rotor 113 rotate and the rotation is transmitted to the second spur gear 115. Further, as shown in FIGS. 1A and 1B, the adjacent drive unit 110 (or finger tip unit 120) is connected to the second spur gear 115. Accordingly, the piezoelectric motor 200 is driven, and thereby, the drive unit 110a and the drive unit 110b or the drive unit 110b and the finger tip unit 120 may be bent or spread.

Figure 5A:
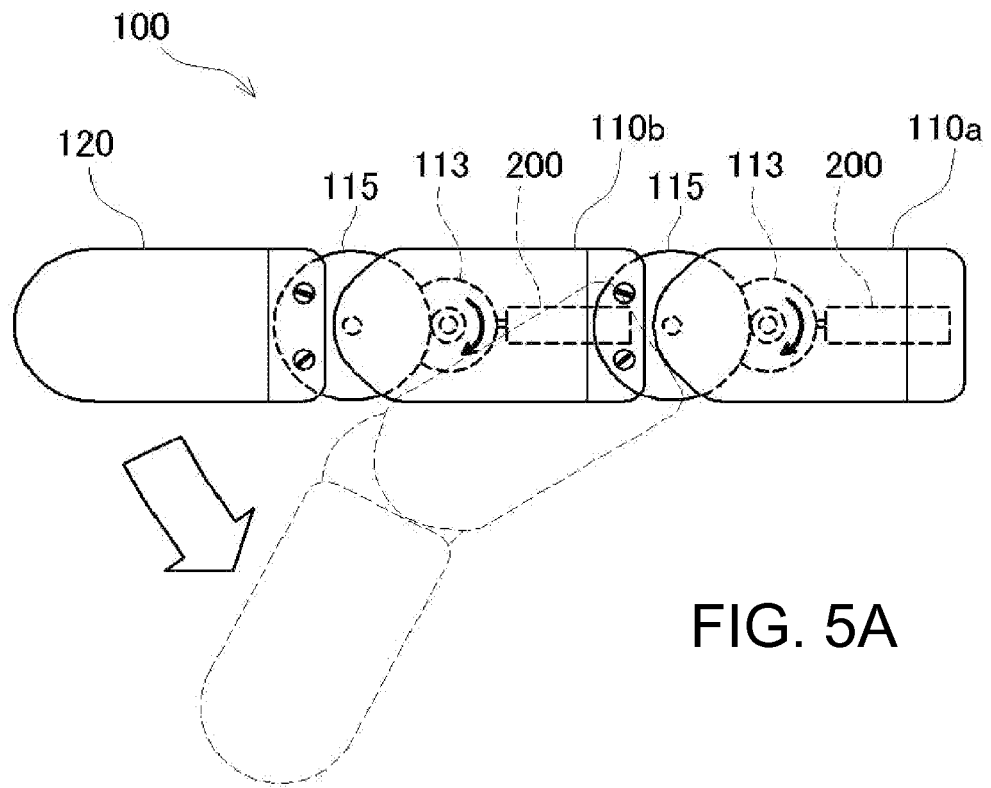
FIGS. 5A and 5B are explanatory diagrams showing movement of the finger assist device.
Figure 5B:
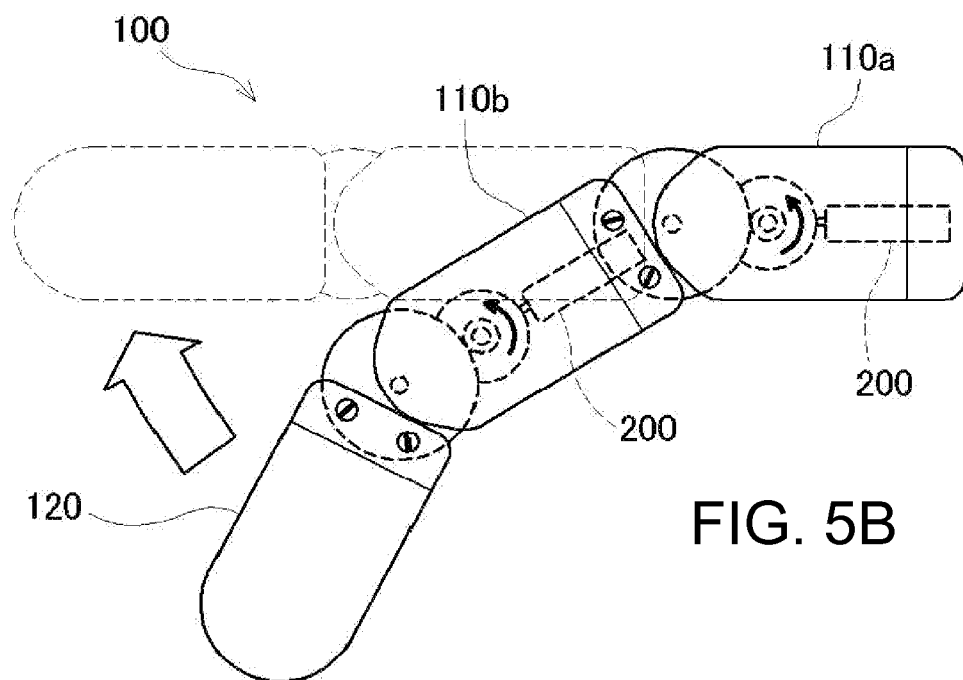

FIGS. 5A and 5B are explanatory diagrams showing movement of the finger assist device 100 of the embodiment. For example, as shown in FIG. 5A, when the piezoelectric motor 200 of the drive unit 110a is driven to rotate the rotor 113 of the drive unit 110a clockwise on the paper surface, the drive unit 110b moves to bend the finger with respect to the drive unit 110a. Similarly, when the piezoelectric motor 200 of the drive unit 110b is driven to rotate the rotor 113 of the drive unit 110b clockwise on the paper surface, the finger tip unit 120 moves to bend with respect to the drive unit 110b. As a result, as shown by a hollow arrow in FIG. 5A, the finger assist device 100 bends.

As shown in FIG. 5B, when the piezoelectric motors 200 of the drive unit 110a and the drive unit 110b are driven in the opposite direction to drive the rotor 113 counterclockwise on the paper surface, as shown by a hollow arrow in the drawing, the finger assist device 100 may be spread (i.e., unbent or straightened).

As described above, the finger assist device 100 of the embodiment may assist the movement of the finger 1 bending or spreading by being worn on the side surface of the finger 1 and driving the piezoelectric motors 200. However, in order to appropriately assist the movement of the finger 1 by the finger assist device 100, it is important to appropriately detect the human's (wearer's) intention that the human wearing the finger assist device 100 on the finger 1 tends to bend or spread the finger 1. Furthermore, even when the wearer bends the finger 1 and the movement is assisted by the finger assist device 100, it is important to detect that the human feels the assistance force weaker or stronger. When the wearer spreads the finger 1, similarly, it is important to detect that the human feels the assistance force of the finger assist device 100 for the finger 1 weaker or stronger. Accordingly, the finger assist device 100 of the embodiment detects the wearer's intention using the output of the first sensor 132b attached to the first nipping portion 130b and the second sensor 132a attached to the second nipping portion 130a.

Figure 6A:
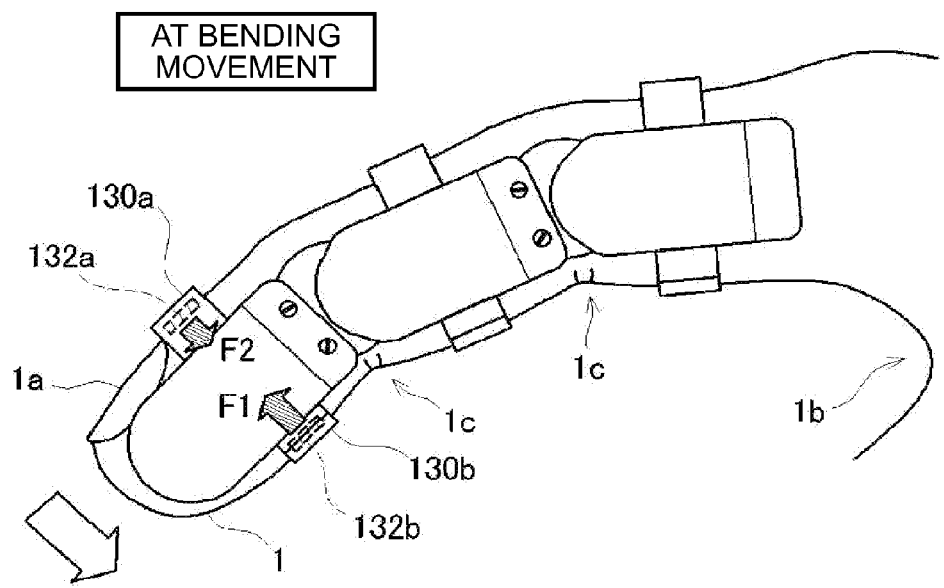
FIGS. 6A and 6B are explanatory diagrams showing an operation principle of detecting an intention of a wearer of the finger assist device based on output of a first sensor and a second sensor.
Figure 6B:
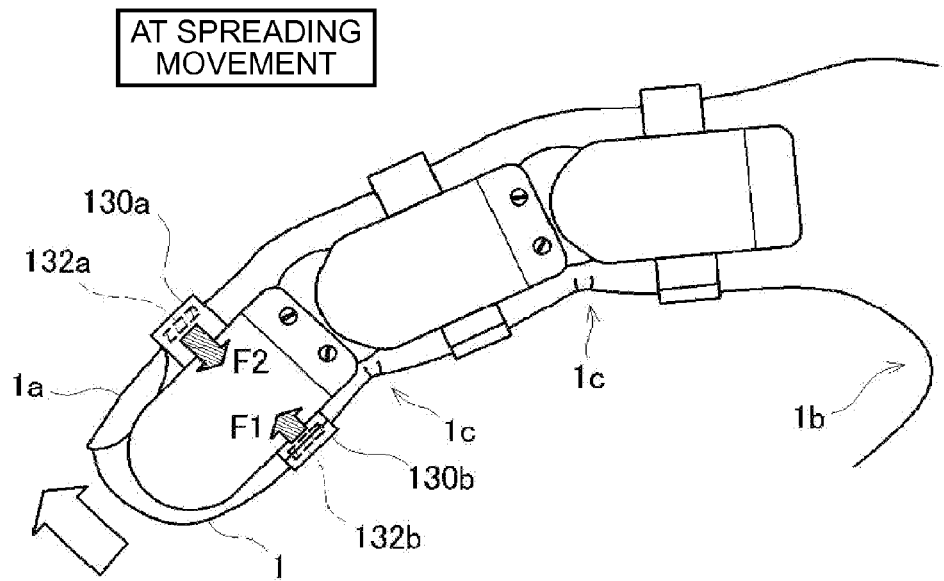

FIGS. 6A and 6B are explanatory diagrams showing a principle of detecting the wearer's intention of the finger assist device 100 of the embodiment based on output of the first sensor 132b and the second sensor 132a. Note that the sign 1a shown in FIGS. 6A and 6B denotes a nail of the finger 1, the sign 1b denotes a fork of the finger 1, and the signs 1c denote joints of the finger 1. As has been described using FIGS. 1A and 1B, when the finger assist device 100 is worn on the finger 1, the first nipping portion 130b nips the finger 1 from the pad of the finger 1 and the second nipping portion 130a nips the finger 1 from the back of the finger 1 while being lightly pressed against the finger 1. Accordingly, contact forces respectively act between the first sensor 132b provided in the first nipping portion 130b and the finger 1 and between the second sensor 132a provided in the second nipping portion 130a and the finger 1. Note that, below, the contact force acting between the first sensor 132b and the finger 1 is referred to as "first contact force" and the contact force acting between the second sensor 132a and the finger 1 is referred to as "second contact force".

Here, as shown in FIG. 6A, the case where the wearer tends to bend the finger 1 is considered. When the operator is bending the finger 1 from the state in which the finger 1 is stationary, the finger 1 of the wearer presses the first nipping portion 130b, and thereby, the first contact force F1 detected by the first sensor 132b increases. Further, the finger 1 of the wearer is separating from the second nipping portion 130a, and thereby, the second contact force F2 detected by the second sensor 132a decreases. Alternatively, if the wearer tends to make the bending force stronger when the finger 1 is bending, the finger 1 of the wearer also presses the first nipping portion 130b. Accordingly, the first contact force F1 detected by the first sensor 132b increases and the second contact force F2 detected by the second sensor 132a decreases.

On the other hand, if the wearer tends to make the bending force weaker when the finger 1 is bending, the wearer weakens the bending force of the finger 1, and, as a result, the movement of the finger tip unit 120 and the drive unit 110 of the finger assist device 100 overtakes the movement of the finger 1 of the wearer. Accordingly, the finger 1 of the wearer presses the second nipping portion 130a, and thereby, the second contact force F2 detected by the second sensor 132a increases and the first contact force F1 detected by the first sensor 132b decreases.

As is clear from the above description, at the bending movement of the finger 1 (including the halt state before bending), when the first contact force F1 detected by the first sensor 132b is larger than the second contact force F2 detected by the second sensor 132a, the finger assist device 100 may increase the force assisting the finger 1 in the bending direction. On the other hand, it is known that, when the first contact force F1 is smaller than the second contact force F2, the finger assist device 100 may decrease the force assisting the finger 1 in the bending direction.

Next, as shown in FIG. 6B, the case where the wearer tends to spread the finger 1 is considered. When the operator is spreading the finger 1 from the state in which the finger 1 is stationary, the finger 1 of the wearer presses the second nipping portion 130a, and thereby, the second contact force F2 detected by the second sensor 132a increases. Further, the finger 1 of the wearer is separating from the first nipping portion 130b, and thereby, the first contact force F1 detected by the first sensor 132b decreases. Alternatively, if the wearer tends to make the spreading force stronger when the finger 1 is spreading, the finger 1 of the wearer also presses the second nipping portion 130a. Accordingly, the second contact force F2 detected by the second sensor 132a increases and the first contact force F1 detected by the first sensor 132b decreases.

On the other hand, if the wearer tends to make the spreading force weaker when the finger 1 is spreading, the wearer weakens the spreading force of the finger 1, and, as a result, the movement of the finger tip unit 120 and the drive unit 110 of the finger assist device 100 overtakes the movement of the finger 1 of the wearer. Accordingly, the finger 1 of the wearer presses the first nipping portion 130b, and thereby, the first contact force F1 detected by the first sensor 132b increases and the second contact force F2 detected by the second sensor 132a decreases.

As is clear from the above description, at the spreading movement of the finger 1 (including the halt state before spreading), when the second contact force F2 detected by the second sensor 132a is larger than the first contact force F1 detected by the first sensor 132b, the finger assist device 100 may increase the force assisting the finger 1 in the spreading direction. On the other hand, it is known that, when the second contact force F2 is smaller than the first contact force F1, the finger assist device 100 may decrease the force assisting the finger 1 in the spreading direction.

In this manner, by comparison between the first contact force F1 detected by the first sensor 132b and the second contact force F2 detected by the second sensor 132a, the drive force of the piezoelectric motor 200 can be increased and decreased according to the intention of the wearer of the finger assist device 100. Accordingly, the bending movement or spreading movement of the finger 1 may be appropriately assisted using the finger assist device 100.

The explanation above has been made while focusing attention on the principle that enables the assist operation according to the wearer's intention by comparison between the first contact force F1 and the second contact force F2. In the case where the principle is applied to the actual control, as the difference between the first contact force F1 and the second contact force F2 is larger, the drive force of the piezoelectric motor 200 may be changed more significantly. Further, if the difference between the first contact force F1 and the second contact force F2 is equal to or less than a predetermined threshold value, the drive force of the piezoelectric motor 200 in this regard may be maintained.

Figure 7:
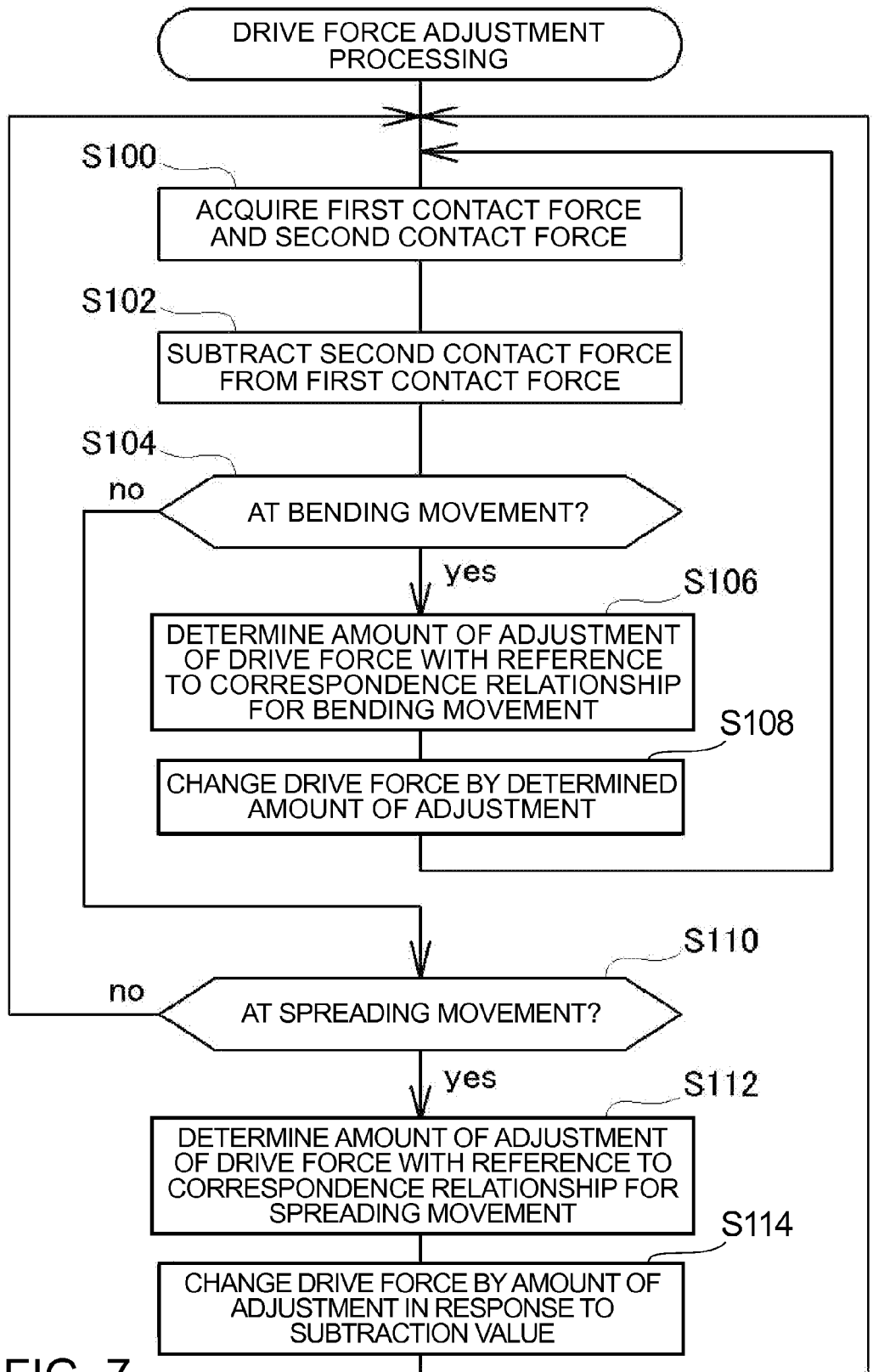
FIG. 7 is a flowchart of drive force adjustment processing of adjusting a drive force of the piezoelectric motor.

FIG. 7 is a flowchart of drive force adjustment processing executed by the finger assist device 100 of the embodiment for adjustment of the drive force of the piezoelectric motor 200 according the wearer's intention. The processing is executed while the drive control part 250 of the finger assist device 100 is driving the piezoelectric motor 200.

As illustrated, in the drive force adjustment processing, first, the first contact force F1 detected by the first sensor 132b and the second contact force F2 detected by the second sensor 132a are acquired (S100), and the second contact force F2 is subtracted from the first contact force F1 (S102). Subsequently, the drive control part 250 determines whether or not the piezoelectric motor 200 is being driven in the bending direction of the finger (see FIG. 5A) (S104). The driving direction of the piezoelectric motor 200 is controlled by the drive control part 250, and thereby, the drive control part 250 may easily determine whether or not the motor is currently being driven in the bending direction of the finger. As a result, if the part determines that the motor is being driven in the bending direction of the finger (S104: yes), the part determines an amount of adjustment of the drive force with reference to a correspondence relationship for bending movement (S106). Here, "correspondence relationship" refers to a correspondence relationship between the subtraction value (=first contact force F1−second contact force F2) and the amount of adjustment of the drive force of the piezoelectric motor 200. In the memory (not shown) of the drive control part 250 of the embodiment, the correspondence relationship for bending movement and a correspondence relationship for spreading movement are stored in advance.

Figure 8A:
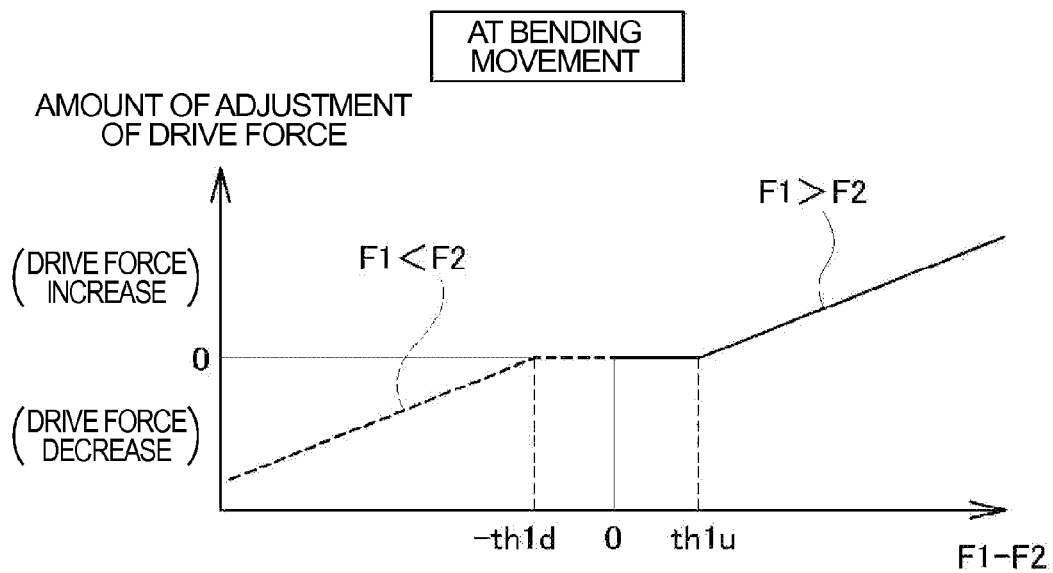
FIGS. 8A and 8B are explanatory diagrams conceptually showing a correspondence relationship for bending movement and a correspondence relationship for spreading movement stored in a memory of a drive control part.
Figure 8B:
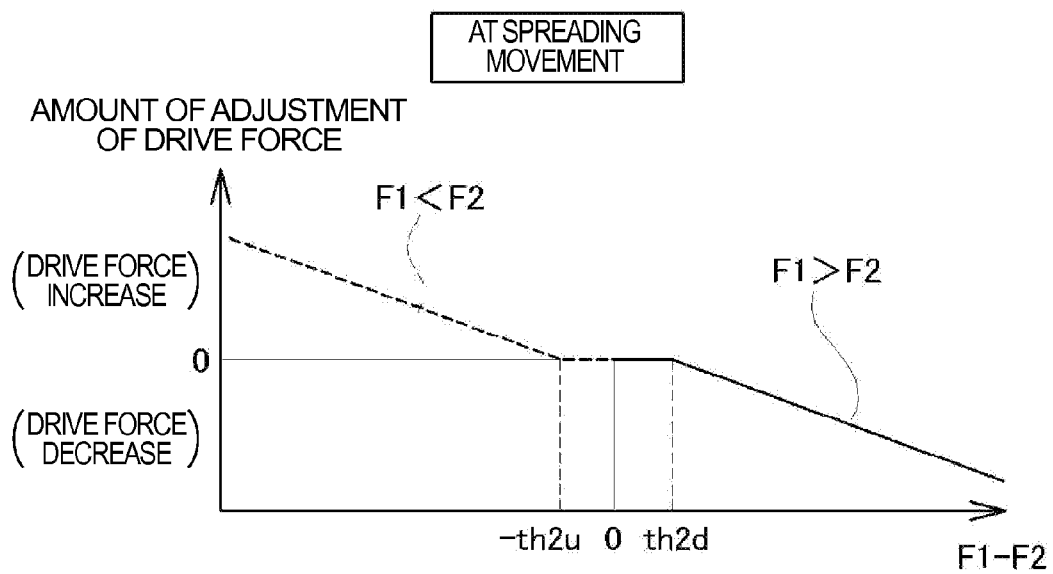

FIGS. 8A and 8B are explanatory diagrams conceptually showing the correspondence relationship for bending movement and the correspondence relationship for spreading movement stored in the memory of the drive control part 250. FIG. 8A shows the correspondence relationship for bending movement and FIG. 8B shows the correspondence relationship for spreading movement. In the correspondence relationship for bending movement shown in FIG. 8A, if the first contact force F1 is larger than the second contact force F2 and an excess amount of the first contact force F1 with respect to the second contact force F2 is less than a first increase-side threshold value th1u or if the second contact force F2 is larger than the first contact force F1 and an excess amount of the second contact force F2 with respect to the first contact force F1 is less than a first decrease-side threshold value th1d, the amount of adjustment of the drive force is set to "0". Accordingly, in either case, the drive force of the piezoelectric motor 200 is maintained without change. Note that the first increase-side threshold value th1u and the first decrease-side threshold value th1d may be set to the same value or different values.

Further, if the first contact force F1 is larger than the second contact force F2, as the subtraction value obtained by subtraction of the second contact force F2 from the first contact force F1 is larger than the first increase-side threshold value th1u, the amount of adjustment of the drive force is set to a larger positive value. Accordingly, during the bending movement, if the first contact force F1 is larger than the second contact force F2 and the subtraction value obtained by subtraction of the second contact force F2 from the first contact force F1 is larger by the first increase-side threshold value th1u or more, as the subtraction value is larger, the drive force is adjusted to increase more significantly.

On the other hand, if the first contact force F1 is smaller than the second contact force F2, as the subtraction value obtained by subtraction of the first contact force F1 from the second contact force F2 is larger than the first decrease-side threshold value th1d, the amount of adjustment of the drive force is set to a negative value having a larger absolute value. Accordingly, during the bending movement, if the second contact force F2 is larger than the first contact force F1 and the subtraction value obtained by subtraction of the first contact force F1 from the second contact force F2 is larger by the first decrease-side threshold value th1d or more, as the subtraction value is larger, the drive force is adjusted to decrease more significantly.

At S106 in FIG. 7, the control part determines the amount of adjustment of the drive force of the piezoelectric motor 200 based on the subtraction value obtained by subtraction of the second contact force F2 from the first contact force F1 as described above. Then, the part adjusts the drive force of the piezoelectric motor 200 using the determined amount of adjustment (S108), then, returns to the head of the processing, and acquires the first contact force F1 and the second contact force F2 again (S100) and performs the subsequent above described series of processing.

On the other hand, if the control part determines that the finger assist device 100 is not in the bending movement at S104 (S104: no), in turn, the part determines whether or not the device is in spreading movement (S110). As a result, if the part determines that the device is in spreading movement (S110: yes), the part determines an amount of adjustment of the drive force with reference to the correspondence relationship for spreading movement (see FIG. 8B) (S112). As shown in FIG. 8B, in the correspondence relationship for spreading movement, if the first contact force F1 is larger than the second contact force F2 and an excess amount of the first contact force F1 with respect to the second contact force F2 is less than a second decrease-side threshold value th2d or if the second contact force F2 is larger than the first contact force F1 and an excess amount of the second contact force F2 with respect to the first contact force F1 is less than a second increase-side threshold value th2u, the amount of adjustment of the drive force is set to "0". Accordingly, in either case, the drive force of the piezoelectric motor 200 is maintained without change. Note that the second decrease-side threshold value th2d and the second increase-side threshold value th2u may be set to the same value or different values.

Further, the second increase-side threshold value th2u used at the spreading movement is set to be a smaller value than that of the first increase-side threshold value th1u used at the bending movement, and similarly, the second decrease-side threshold value th2d used at the spreading movement is set to be a smaller value than that of the first decrease-side threshold value th1d used at the bending movement. This is because the force of the first finger 1 is weaker at spreading than that at bending and the finger assist device 100 may assist the finger 1 from when the force of the first finger 1 is smaller.

Furthermore, if the first contact force F1 is larger than the second contact force F2, as the subtraction value obtained by subtraction of the second contact force F2 from the first contact force F1 is larger than the second decrease-side threshold value th2d, the amount of adjustment of the drive force is set to a negative value having a larger absolute value. Accordingly, during the spreading movement, if the first contact force F1 is larger than the second contact force F2 and the subtraction value obtained by subtraction of the second contact force F2 from the first contact force F1 is larger by the second decrease-side threshold value th2d or more, as the subtraction value is larger, the drive force is adjusted to decrease more significantly.

On the other hand, if the first contact force F1 is smaller than the second contact force F2, as the subtraction value obtained by subtraction of the first contact force F1 from the second contact force F2 is larger than the second increase-side threshold value th2u, the amount of adjustment of the drive force is set to a larger positive value. Accordingly, during the spreading movement, if the second contact force F2 is larger than the first contact force F1 and the subtraction value obtained by subtraction of the first contact force F1 from the second contact force F2 is larger by the second increase-side threshold value th2u or more, as the subtraction value is larger, the drive force is adjusted to increase more significantly.

At S112 in FIG. 7, the control part determines the amount of adjustment of the drive force of the piezoelectric motor 200 based on the subtraction value obtained by subtraction of the second contact force F2 from the first contact force F1 as described above. Then, the part adjusts the drive force of the piezoelectric motor 200 using the determined amount of adjustment (S114), then, returns to the head of the processing, and acquires the first contact force F1 and the second contact force F2 again (S100) and performs the subsequent above described series of processing. Further, if the part determines that the device is not in the spreading movement at S110 (S110, no), the part directly returns to the head, and acquires the first contact force F1 and the second contact force F2 again (S100) and continues the subsequent above described series of processing.

The finger assist device 100 of the embodiment adjusts the drive force of the piezoelectric motor 200 based on the first contact force F1 detected by the first sensor 132b and the second contact force F2 detected by the second sensor 132a. Since the intention of the wearer of the finger assist device 100 appears in the value of the difference between the first contact force F1 and the second contact force F2, the bending movement and the spreading movement of the finger 1 may be appropriately assisted using the finger assist device 100 according to the wearer's intention.

There are several modified examples of the finger assist device 100 of the embodiment. Below, these modified examples will be briefly explained with attention focused on the differences from the embodiment. Note that, in the following modified examples, the parts in common with the embodiment have the same signs and their detailed explanation will be omitted.

In the above described embodiment, the explanation that the first nipping portion 130b on the pad of the finger 1 is formed using the more deformable material than that of the second nipping portion 130a on the back of the finger 1 has been made (see FIG. 1C). However, the first nipping portion 130b may be formed using a non-deformable material such as metal or hard resin like the second nipping portion 130a.

Figure 9:
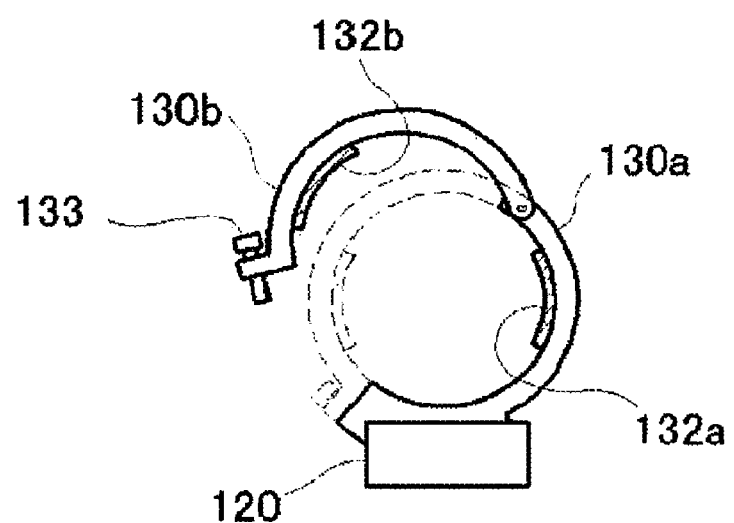
FIG. 9 is an explanatory diagram exemplifying a first nipping portion and a second nipping portion of a first modified example.

FIG. 9 is an explanatory diagram exemplifying the first nipping portion 130b and the second nipping portion 130a of a first modified example. Note that, in FIG. 9, the first nipping portion 130b and the second nipping portion 130a of the finger tip unit 120 are shown, however, the first nipping portion 130b and the second nipping portion 130a may be used for the drive unit 110.

In the illustrated first modified example, both the first nipping portion 130b and the second nipping portion 130a are formed to have nearly semi-circular arc shapes, and one end of the first nipping portion 130b is rotatably and axially supported with respect to one end of the second nipping portion 130a. Accordingly, by rotation of the first nipping portion 130b, the state in which the first nipping portion 130b is opened with respect to the second nipping portion 130a (state shown by solid lines in the drawing) and the state in which the first nipping portion 130b is closed with respect to the second nipping portion 130a (state shown by broken lines in the drawing) may be obtained. Further, while the first nipping portion 130b is opened, the inside of the second nipping portion 130a is brought into contact with the back of the finger 1 and the first nipping portion 130b is rotated to be closed with respect to the second nipping portion 130a, and then, the first nipping portion 130b is fixed to the second nipping portion 130a using a securement screw 133 provided at the other end of the first nipping portion 130b. In this manner, the finger 1 may be nipped (e.g., lightly squeezed) with the first sensor 132b of the first nipping portion 130b pressed against the pad of the finger 1 and the second sensor 132a of the second nipping portion 130a pressed against the back of the finger 1.

Figure 10A:
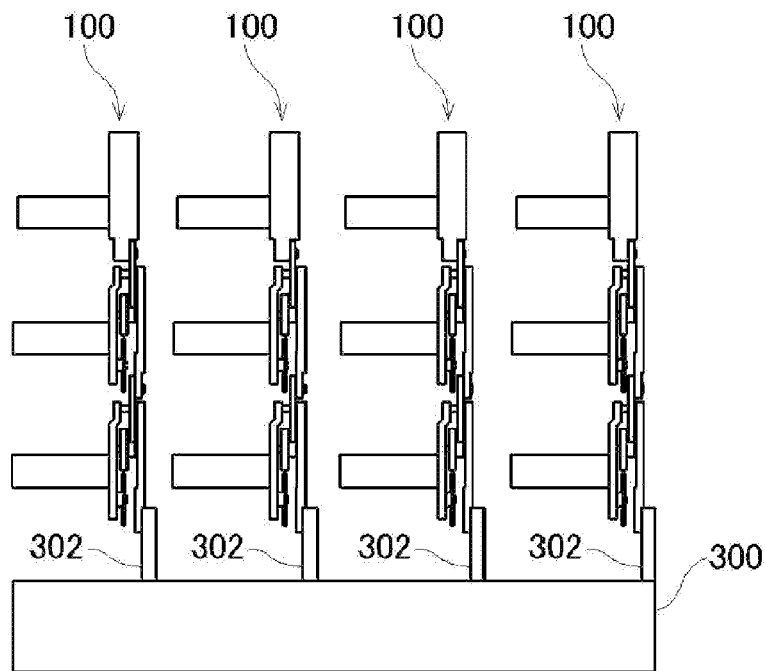
FIGS. 10A and 10B are explanatory diagrams exemplifying a second modified example in which a plurality of finger assist devices are attached to attachment members in parallel.
Figure 10B:
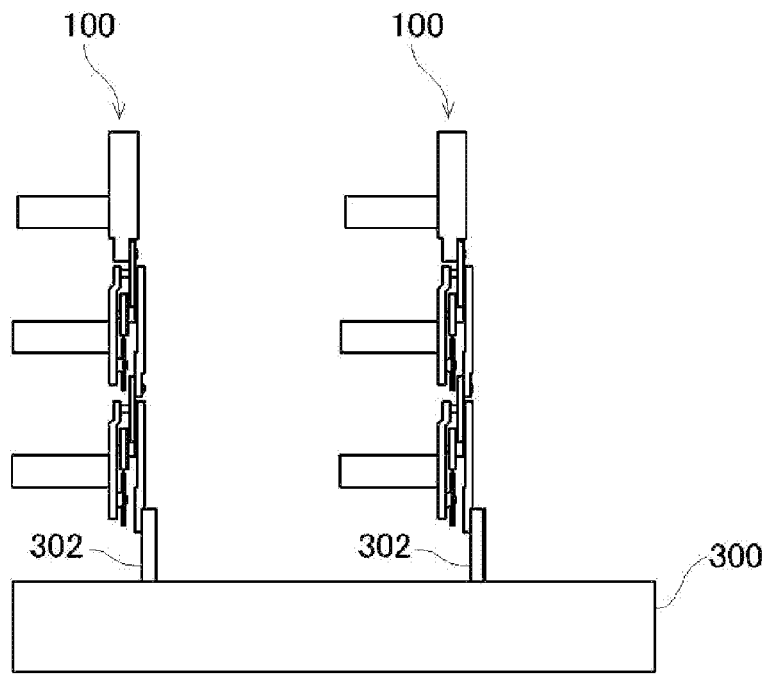

FIGS. 10A and 10B are explanatory diagrams exemplifying a second modified example in which a plurality of finger assist devices 100 are attached to attachment members 300 in parallel. In the second modified example, the respective finger assist devices 100 are attached via attachment parts 302 to the attachment members 300 in parallel. In the second modified example, the attachment member 300 is worn on a palm or back of a hand, and thereby, the finger assist device 100 may be worn in an appropriate position with respect to the finger 1. Accordingly, the bending movement of the finger 1 may be appropriately assisted.

Note that, in the example shown in FIG. 10A, the four finger assist devices 100 are attached to the attachment member 300, and the bending movement of the four fingers 1 of the index finger, the middle finger, the ring finger, and the little finger may be assisted. Obviously, one more finger assist device 100 may be attached to the attachment member 300 so that the bending movement of the thumb may be assisted. Further, as exemplified in FIG. 10B, the finger assist devices 100 may be attached to the attachment member 300 only for the fingers 1 that require assistance.

The finger assist devices 100 of the embodiment and the modified examples have been explained, however, the invention is not limited to the above embodiment or modified examples, but may be implemented in various forms without departing from the scope thereof.

The entire disclosure of Japanese Patent Application No. 2013-061543 filed Mar. 25, 2013 is expressly incorporated by reference herein.

What is claimed is:

1. A finger assist device assisting movement of a finger comprising:
    a nipper adapted to be worn on the finger;
    a plurality of units rotatably connected to one another in a bending direction, at least one of the units being coupled to the nipper;
    a sensor provided in the nipper to detect a contact force generated toward the nipper;
    a driver drivably connected to the plurality of units to impart relative rotation thereto; and
    a drive force controller operatively associated with the sensor and driver, the controller being configured to control a drive force of the driver in response to the contact force detected by the sensor,
    wherein the sensor includes a first sensor that detects a first contact force generated in the bending direction and a second sensor that detects a second contact force generated in a spreading direction opposite the bending direction, wherein the drive force controller being configured to increase the drive force for rotating the units in the bending direction if the first contact force is larger than the second contact force, and to decrease the drive force for rotating the units in the bending direction if the first contact force is smaller than the second contact force.

2. The finger assist device according to claim 1, wherein, the drive force controller is further configured to increase the drive force in the bending direction if the first contact force is larger than the second contact force by a first increase threshold value or more, and to decrease the drive force in the bending direction if the second contact force is larger than the first contact force by a first decrease threshold value, and the drive force controller is also configured to maintain the drive force in the bending direction if the first contact force is larger than the second contact force and an excess amount of the first contact force with respect to the second contact force is less than the first increase threshold value or the second contact force is larger than the first contact force and an excess amount of the second contact force with respect to the first contact force is less than the first decrease threshold value.

3. The finger assist device according to claim 1, wherein, the drive force controller is configured to decrease the drive force in the spreading direction if the first contact force is larger than the second contact force, and to increase the drive force in the spreading direction if the second contact force is larger than the first contact force.

4. The finger assist device according to claim 3, wherein, the drive force controller is also configured to decrease the drive force in the spreading direction if the first contact force is larger than the second contact force by a predetermined second decrease threshold value or more, and to increase the drive force in the spreading direction if the second contact force is larger than the first contact force by a second increase threshold value, and the drive force controller is also configured to maintain the drive force in the spreading direction if the first contact force is larger than the second contact force and an excess amount of the first contact force with respect to the second contact force is less than the second decrease threshold value, or the second contact force is larger than the first contact force and an excess amount of the second contact force with respect to the first contact force is less than the second increase threshold value.

5. The finger assist device according to claim 4, wherein, the second increase threshold value is a value smaller than the first increase threshold value, and the second decrease threshold value is a value smaller than the first decrease threshold value.

6. The finger assist device according to claim 1, wherein, the first sensor and the second sensor are provided at a tip end side of the nipper.

7. The finger assist device according to claim 1, wherein, the nipper includes a first nipping member provided on a bending direction side of the nipper and a second nipping member provided on a spreading direction side of the nipper, and the first nipping member is more deformable than the second nipping member.

8. The finger assist device according to claim 1, wherein the driver is a vibrator containing a piezoelectric material.

9. A finger assist device assisting movement of a finger comprising:
 a band adapted to be worn on the finger;
 a pressure sensor on an inner periphery of the band;
 a first link connected to the band;
 a second link rotatably connected to the first link at a joint;
 a driver connected to the joint and operable to selectively impart relative rotation between the first and second links; and a controller communicating with the sensor and driver, the controller being configured to control a drive force of the driver in response to feedback from the sensor, wherein the sensor includes a first sensor that detects a first contact force generated in the bending direction and a second sensor that detects a second contact force generated in a spreading direction opposite the bending direction, wherein the controller is configured to: increase the drive force for rotating in the bending direction if the first contact force is larger than the second contact force, and decrease the drive force for rotating in the bending direction if the first contact force is smaller than the second contact force.

10. The finger assist device according to claim 9, wherein, the controller is further configured to increase the drive force in the bending direction if the first contact force is larger than the second contact force by a first increase threshold value or more, and to decrease the drive force in the bending direction if the second contact force is larger than the first contact force by a first decrease threshold value, and the controller is also configured to maintain the drive force in the bending direction if the first contact force is larger than the second contact force and an excess amount of the first contact force with respect to the second contact force is less than the first increase threshold value or the second contact force is larger than the first contact force and an excess amount of the second contact force with respect to the first contact force is less than the first decrease threshold value.

11. The finger assist device according to claim 9, wherein, the controller is configured to:
 decrease the drive force in the unbending direction if the first contact force is larger than the second contact force, and
 increase the drive force in the unbending direction if the second contact force is larger than the first contact force.

12. The finger assist device according to claim 11, wherein,
 the controller is also configured to decrease the drive force in the spreading direction if the first contact force is larger than the second contact force by a predetermined second decrease threshold value or more, and to increase the drive force in the spreading direction if the second contact force is larger than the first contact force by a second increase threshold value, and
 the controller is also configured to maintain the drive force in the spreading direction if the first contact force is larger than the second contact force and an excess amount of the first contact force with respect to the second contact force is less than the second decrease threshold value, or the second contact force is larger than the first contact force and an excess amount of the second contact force with respect to the first contact force is less than the second increase threshold value.

13. The finger assist device according to claim 9, wherein the driver is a vibrator containing a piezoelectric material.

14. A method of assisting movement of a finger comprising:
 providing a finger assist device including:
 a band adapted to be worn on the finger;
 a pressure sensor on an inner periphery of the band, the sensor having:
 a first sensor that detects a first contact force generated in a bending direction; and a second sensor that detects a second contact force generated in an unbending direction opposite the bending direction;
a first link connected to the band;
a second link rotatably connected to the first link at a joint; and
a driver connected to the joint and operable to selectively impart relative rotation between the first and second links; and
controlling a drive force of the driver in response to feedback from the sensor;
wherein said controlling includes:
increasing the drive force for rotating in the bending direction if the first contact force is larger than the second contact force;
decreasing the drive force for rotating in the bending direction if the first contact force is smaller than the second contact force;
decreasing the drive force in the unbending direction if the first contact force is larger than the second contact force; and
increasing the drive force in the unbending direction if the second contact force is larger than the first contact force.

15. The method according to claim 14, wherein the controlling further comprises:
increasing the drive force in the bending direction if the first contact force is larger than the second contact force by a first increase threshold value or more;
decreasing the drive force in the bending direction if the second contact force is larger than the first contact force by a first decrease threshold value; and
maintaining the drive force in the bending direction if the first contact force is larger than the second contact force and an excess amount of the first contact force with respect to the second contact force is less than the first increase threshold value or the second contact force is larger than the first contact force and an excess amount of the second contact force with respect to the first contact force is less than the first decrease threshold value.

16. The method according to claim 14, wherein the controlling further comprises:
decreasing the drive force in the spreading direction if the first contact force is larger than the second contact force by a predetermined second decrease threshold value or more;
increasing the drive force in the spreading direction if the second contact force is larger than the first contact force by a second increase threshold value; and
maintaining the drive force in the spreading direction if the first contact force is larger than the second contact force and an excess amount of the first contact force with respect to the second contact force is less than the second decrease threshold value, or the second contact force is larger than the first contact force and an excess amount of the second contact force with respect to the first contact force is less than the second increase threshold value.

17. The method according to claim 14, wherein the driver is a vibrator containing a piezoelectric material.

* * * * *